United States Patent [19]

Yarosh

[11] Patent Number: 5,407,804
[45] Date of Patent: Apr. 18, 1995

[54] ASSAYS FOR $O^6$-METHYLGUANINE-DNA METHYLTRANSFERASE

[75] Inventor: Daniel B. Yarosh, Merrick, N.Y.

[73] Assignee: Applied Genetics Inc., Freeport, N.Y.

[21] Appl. No.: 887,733

[22] Filed: May 22, 1992

[51] Int. Cl.$^6$ .................. C12Q 1/00; C12N 5/20; C07K 15/28; G01N 33/533

[52] U.S. Cl. ................... 435/7.4; 435/7.21; 435/7.92; 435/7.95; 435/70.21; 435/240.27; 435/960; 435/193; 530/388.26

[58] Field of Search ............ 435/7.1, 7.21, 7.4, 435/7.95, 7.52, 70.21, 240.27, 193, 196, 960; 436/548; 530/388.26; 935/104, 110

[56] References Cited

U.S. PATENT DOCUMENTS

| | | | |
|---|---|---|---|
| 5,077,211 | 12/1991 | Yarosh | 435/193 |
| 5,272,079 | 12/1993 | Yarosh | 435/193 |
| 5,296,231 | 3/1994 | Yarosh | 424/450 |

FOREIGN PATENT DOCUMENTS

WO90/00598 1/1990 WIPO.

OTHER PUBLICATIONS

Herlow et al (1988) Antibodies: A Laboratory Manual, Cold Spring Harbor Press, Cold Spring Harbor, N.Y., pp. 72-77, 92-97, 128-135 & 141-157.

Goding (1983) "Monoclonel Antibodies: Principles and Practice", Academic Press, Orlando, pp. 56-91, 212-218 & 234-239.

Inoue (1986) "Video Microscopy" Plenum Press, New York, pp. 327-403 and 415-416.

Ayi, et al., "Interacellular Localization of Human DNA Repair Enzyme Methylguanine-DNA Methyltransferase by Antibodies and Its Importance," Cancer Research, 1992, 52:6423-6430.

Lee, et al., "Immunohistological examination of the inter- and intracellular distribution of $O^6$-alkylguanine DNA-alkyltransferase in human liver and melanoma," Br. J. Cancer, 1992, 66:355-360.

Lee, et al., "Expression of $O^6$-Alkylguanine-DNA-Alkyltransferase in situ in Ovarian and Hodgkin's Tumours," Eur. J. Cancer, 1993, 9:1306-1312.

Rafferty, et al., "Isolation and partial characterisation of a Chinese hamster $O^6$-alkylguanine DNA alkyltransferase cDNA", Nucleic Acids Research, 1992, 20:1891-1895.

Wu, et al., "Expression of Human $O^6$-Methylguanine-DNA Methyltransferase in Chinese Hamster Ovary Cells and Restoration of Cellular Resistance to Certain N-Nitroso Compounds," Molecular Carcinogenesis, 1991, 4:482-488.

Yarosh, D., "The Role of $O^6$-Methylguanine-DNA Methyltransferase in Cell Survival, Mutagenesis and Carcinogenesis", Mutation Reseach, vol. 145, pp. 1-16, 1985.

Pegg, A. E., "Properties of Mammalian $O^6$-Alkylguanine-DNA Alkyltransferase", Mutation Research, vol. 233, pp. 165-175, 1990.

Pegg, A. E., "Mammalian $O^6$-Alkylguanine-DNA Alkyltransferase: Regulation and Importance in Response to Alkylating, Carcinogenic and Therapeutic Agents", Cancer Research, vol. 50, pp. 6119-6129, 1990.

(List continued on next page.)

Primary Examiner—David L. Lacey
Assistant Examiner—Jacqueline G. Krikorian
Attorney, Agent, or Firm—Maurice M. Klee

[57] ABSTRACT

Assays for the DNA repair protein $O^6$-methylguanine-DNA methyltransferase (MGMT) are provided which employ monoclonal antibodies prepared using MGMT having transferase activity, as opposed to denatured MGMT or MGMT fragments. The monoclonal antibodies are able to recognize MGMT in single cell preparations (immunohistochemical staining assays) and in cell extracts (immunoassays). In connection with immunohistochemical staining, the use of a fluorescent readout coupled with digitization of the cell image allows for quantitative measures of MGMT levels in, for example, tumor biopsy samples. Such quantitative measures can be used to determine which patients are likely to benefit from chemotherapy using alkylating agents since tumor cells having low MGMT levels are more likely to be killed by such agents than those with high MGMT levels.

8 Claims, 4 Drawing Sheets

OTHER PUBLICATIONS

Watatani, W., et al., "Analysis of N-Methyl-N'-Nitro-N-Nitrosoguanidine (MNNG)-Induced DNA Damage in Tumor Cell Strains from Japanese Patients and Demonstration of MNNG Hypersensitivity of MER⁻ Xenografts in Athymic Nude Mice", *Carcinogenesis*, vol. 6, pp. 549-553, 1985.

Aida, T., et al., "Inhibition of $O^6$-Alkylguanine-DNA Alkyltransferase Activity Potentiates Cytotoxicity and Induction of SCEs in Human Glioma Cells Resistant to 1,3-Bis(2-Chloroethyl)-1-Nitrosourea", *Carcinogenesis*, vol. 8, pp. 1219-1223, 1987.

Fujio, C., et al., "Hypersensitivity of Human Tumor Xenografts Lacking $O^6$-Alkylguanine-DNA Alkyltransferase to the Anti-Tumor Agent 1-(-4-Amino-2-Methyl-5-Pyrimidinyl) Methyl-3-(2-Chloroethyl)-3-Nitrosourea", *Carcinogenesis*, vol. 10, pp. 351-356, 1989.

Brent, T., "Isolation and Purification of $O^6$-Alkylguinanine-DNA Alkyltransferase from Human Leukemic Cells. Prevention of Chloroethylnitrosourea-Induced Cross-Links by Purified Enzyme", *Pharmacological Therapeutics*, vol. 31, pp. 121-139, 1985.

Von Wronski, M., et al., "Monoclonal Antibodies Against Human $O^6$-Alkylguanine-DNA Alkyltransferase", Abstract in *Proceedings of the American Association for Cancer Research*, vol. 30, pp. 486, 1989.

Brent, T., et al., "Immunoaffinity Purification of Human $O^6$-Methylguanine-DNA Methyltransferase Using Newly Developed Monoclonal Antibodies", *Cancer Research*, vol. 50, pp. 58-61, 1990.

Von Wronski, M., et al., "Expression of $O^6$-Alkylguanine-DNA Alkyltransferase in MER+ and MER⁻ Human Cell Extracts Probed with Specific Monoclonal Antibodies", *Cancer Communications*, vol. 1, pp. 323-327, 1989.

Yarosh, D., et al., "Monoclonal Antibodies Against the Human $O^6$-Methylguanine-DNA Methyltransferase", Abstract in *Proceedings of the American Association for Cancer Research*, vol. 29, p. 1, 1988.

Ostrowski, L., et al., "Production and Characterization of Antipeptide Antibodies Against Human $O^6$-Methylguanine-DNA Methyltransferase", *Cancer Research*, vol. 51, pp. 3339-3344, 1991.

Pegg, A. E., et al., "Production of Antibodies to Peptide Sequences Present in Human $O^6$-Alkylguanine-DNA Alkyltransferase and Their Use to Detect this Protein in Cell Extracts", *Carcinogenesis*, vol. 12, No. 9, pp. 1671-1677, 1991.

Pegg, A. E., et al., "Use of Antibodies to Human $O^6$-Alkylguanine-DNA Alkyltransferase to Study the Content of this Protein in Cells Treated with $O^6$-Benzylguanine or N-Methyl-N'-Nitro-N-Nitrosoguanidine", *Carcinogenesis*, vol. 12, No. 9, pp. 1679-1683, 1991.

Lee, S. M., et al., "Regional and Cellular Heterogeneity of Expression of $O^6$-Alkylguanine-DNA Alkyltransferase in Melanoma", Abstract in *Proceedings of the American Association for Cancer Research*, vol. 33, Mar. 1992, p. 547.

Pegg, A. E., et al., "Repair of DNA Containing $O^6$-Alkylguanine", *Federation of American Societies of Experimental Biology Journal*, vol. 6, Mar. 1992, pp. 2302-2310.

Campbell, A. M., *Monoclonal Antibody Technology: The Production and Characterization of Rodent and Human Hybridomas*, Elsevier, N.Y., 1984, pp. 88-89.

Goding, J. W., *Monoclonal Antibodies: Principles and Practice*, Harcourt Brace Jovanovich, New York, 1986, pp. 28-31.

Tano, K., et al., "Isolation and Structural Characterization of a cDNA Clone Encoding the Human DNA Repair Protein for $O^6$-Alkylguanine", *Proc. Natl. Acad. Sci. USA*, vol. 87, pp. 686-690, 1990.

Hayakawa, H., et al., "Expression and Cloning of Complementary DNA for a Human Enzyme that Repair $O^6$-Methylguanine in DNA", *J. Mol. Biol.*, vol. 213, pp. 739-747, 1991.

Rydberg, B., et al., "cDNA Cloning and Chromosomal Assignment of the Human $O^6$-Methylguanine-DNA Methyltransferase", *J. Biol. Chem.*, vol. 265, pp. 9563-9569, 1990.

Von Wronski, M. A., et al., "Structural and Immunological Comparison of Indigenous Human $O^6$-Methylguanine-DNA Methyltransferase with that Encoded by a Cloned cDNA", *J. Biol. Chem.*, vol. 266, pp. 1064-1070, 1991.

Shiota, S., et al., "Characterization of cDNA Encoding Mouse DNA Repair Protein $O^6$-Methylguanine-DNA Methyltransferase and High-Level Expression of the Wild-Type and Mutant Proteins in *Escherichia coli.*," *Biochemistry* 31:1897-1903, 1992.

Sakumi, N., et al., "Cloning and Expression of cDNA for Rat $O^6$-Methylguanine-DNA Methyltransferase," *Nucleic Acids Research*, 19:5597-5601, 1991.

Rydberg, B., et al., "Active Site Amino Acid Sequence of the Bovine $O^6$-Methylguanine-DNA Methyltransferase", *Nucleic Acids Res.*, vol. 18, pp. 17-21, 1990.

Kohler, et al., *Nature*, vol. 256, pp. 495-497, 1975.

ASSAYS FOR O$^6$-METHYLGUANINE-DNA METHYLTRANSFERASE

FIELD OF THE INVENTION

This invention relates to the DNA repair proteins known as O$^6$-methylguanine-DNA methyltransferase (MGMT) and, in particular, to assays for detecting MGMT in a variety of biological preparations, including, most importantly, preparations containing single cells, e.g., cells fixed to microscope slides.

BACKGROUND OF THE INVENTION

The MGMTs (EC 2.1.1.63; also referred to in the art as O$^6$-alkylguanine-DNA alkyltransferases) are DNA repair proteins found in most living organisms which transfer alkyl groups from the O-6 position of guanine in alkylated DNA to a cysteine residue of their own polypeptide chains, thereby becoming catalytically inactive. Since each MGMT molecule acts but once, the repair capacity of a living cell is determined by the number of MGMT molecules in a cell at the time of DNA alkylation, and the rate of its resynthesis.

The MGMT levels of living cells are directly correlated with the response of those cells to $S_n2$ alkylating agents, such as the clinically useful anti-cancer chemotherapeutic drug group, the chloroethylnitrosoureas. A group of human tumors and cell strains have the MER$^-$ phenotype and are deficient in MGMT activity, and these tumors and cells are extremely sensitive to killing by these drugs.

Various reviews of the MGMTs and their activity have appeared in the literature, including: DANIEL B. YAROSH, "THE ROLE OF O$^6$-METHYLGUANINE-DNA METHYLTRANSFERASE IN CELL SURVIVAL, MUTAGENESIS AND CARCINOGENESIS", *MUTATION RESEARCH*, VOLUME 145, PAGES 1-16, 1985; ANTHONY E. PEGG, "PROPERTIES OF MAMMALIAN O$^6$-ALKYLGUANINE-DNA ALKYLTRANSFERASE, *MUTATION RESEARCH*, VOLUME 233, PAGES 165-175, 1990; and ANTHONY E. PEGG, "MAMMALIAN O$^6$-ALKYLGUANINE-DNA ALKYLTRANSFERASE: REGULATION AND IMPORTANCE IN RESPONSE TO ALKYLATING, CARCINOGENIC AND THERAPEUTIC AGENTS", *CANCER RESEARCH*, VOLUME 50, PAGES 6119-6129, 1990, the relevant portions of which are incorporated herein by reference.

Scientists in the field have long recognized that measurement of MGMT levels in human tumors would be an important contribution to improving chloroethylnitrosourea chemotherapy of cancer. For example, M. Watatani, M. Ikenaga, T. Hatanaka, M. Kinuta, S. Takai, T. Mori and S. Kondo predicted in 1985 that "If the MER$^-$ phenotype could be detected by some means in biopsy specimens, it should be possible to cure this type of malignant tumor by appropriate chemotherapy." See "ANALYSIS OF N-METHYL-N'-NITRO-N-NITROSOGUANIDINE (MNNG)-INDUCED DNA DAMAGE IN TUMOR CELL STRAINS FROM JAPANESE PATIENTS AND DEMONSTRATION OF MNNG HYPERSENSITIVITY OF MER$^-$ XENOGRAFTS IN ATHYMIC NUDE MICE", *CARCINOGENESIS*, VOLUME 6, PAGES 549-553 at 552, 1985.

Similarly, T. Aida, R. Cheitlin and W. Bodell wrote in 1987: "Our results suggest that measurement of O$^6$-AT [MGMT] activity in human brain tumor biopsy specimens may be a good prognostic indicator of clinical resistance to BCNU [a chloroethylnitrosourea chemotherapy agent]." See "INHIBITION OF O$^6$-ALKYLGUANINE-DNA ALKYLTRANSFERASE ACTIVITY POTENTIATES CYTOTOXICITY AND INDUCTION OF SCEs IN HUMAN GLIOMA CELLS RESISTANT TO 1,3-BIS(2-CHLOROETHYL)-1-NITROSOUREA", *CARCINOGENESIS*, VOLUME 8, PAGES 1219-1223 at 1222, 1987.

Along these same lines, C. Fujio, H. R. Chang, T. Tsujimura, K. Ishizaki, H. Kitamura, and M. Ikenaga concluded in 1989 that "measurement of ATR [MGMT] activity in biopsy specimens may provide a useful guide to predict the response to chemotherapy" and, in particular, that "MER tumors may be efficiently cured by treatment with alkylating agents, including ACNU, provided that we could detect the MER$^-$ tumors at their early stage of development." These authors also point out that about one-fifth of human tumor cell strains established in the United States show a MER$^-$ phenotype and that similarly, a MER$^-$ frequency of 15% has been found in tumor cell lines derived from Japanese patients. See "HYPERSENSITIVITY OF HUMAN TUMOR XENOGRAFTS LACKING O$^6$-ALKYLGUANINE-DNA ALKYLTRANSFERASE TO THE ANTI-TUMOR AGENT 1-(4-AMINO-2-METHYL-5-PYRIMIDINYL) METHYL-3-(2-CHLOROETHYL)-3- NITROSOUREA", *CARCINOGENESIS*, VOLUME 10, PAGES 351-356 at 351 and 355, 1989.

Prior to the present invention, the most sensitive assay for MGMT was an activity assay, which measured the transfer of alkyl groups from DNA to the MGMT protein. This assay, however, relies on collecting fresh samples, and invariably includes irrelevant cells along with relevant cells in the extract used for assay. For years, it has been recognized in the art that an immunoassay for MGMT levels in single cell preparations would represent an important and essential improvement having great clinical relevance.

Thus, in 1985, Thomas Brent, a leading researcher in this field described the problems with activity measurements and the need for an immunoassay as follows: "In practice, however, due to cellular heterogeneity and necrosis, transferase activity measurements in human tumor biopsies are fraught with difficulty. The development of an antibody for the human alkyltransferase and a cytological immunoassay for the transfer protein in tumor cells should enable these predictive assays to be achieved." See "ISOLATION AND PURIFICATION OF O$^6$-ALKYLGUANINE-DNA ALKYLTRANSFERASE FROM HUMAN LEUKEMIC CELLS. PREVENTION OF CHLOROETHYLNITROSOUREA-INDUCED CROSS-LINKS BY PURIFIED ENZYME", PHARMACOLOGICAL THERAPEUTICS, VOLUME 31, PAGES 121-139 at 138, 1985.

In view of this clear need for an immunoassay and, in particular, a single cell immunoassay, substantial efforts by a variety of groups throughout the world have been made to develop antibodies to MGMT. Notwithstanding these efforts, prior to the present invention, truly useful and practical antibodies to MGMT, in particular, monoclonal antibodies, have not been found. As discussed below, this failure by the leading groups to satisfy this long felt need has resulted from the approaches they took in selecting immunizing materials, i.e., the groups did not use MGMT having transferase activity as their immunizing material.

Thus, the Bigner/Brent group reported the development of monoclonal antibodies using denatured MGMT, i.e., MGMT which had been purified using polyacrylamide-SDS gels and thus lacked transferase activity. The antibodies were only able to recognize MGMT after denaturation by SDS and were thus unsuitable for use in single cell assays. See M. VON WRONSKI, T. BRENT, C. PEGRAM, D. BIGNER, "MONOCLONAL ANTIBODIES AGAINST HUMAN $O^6$-ALKYLGUANINE-DNA ALKYLTRANSFERASE", *PROCEEDINGS OF THE AMERICAN ASSOCIATION FOR CANCER RESEARCH*, VOLUME 30, PAGE 486, 1989; and T. BRENT, M. VON WRONSKI, C. PEGRAM AND D. BIGNER, "IMMUNOAFFINITY PURIFICATION OF HUMAN $O^6$-METHYLGUANINE-DNA METHYLTRANSFERASE USING NEWLY DEVELOPED MONOCLONAL ANTIBODIES", CANCER RESEARCH, VOLUME 50, PAGES 58–61, 1990. See also, M. VON WRONSKI, D. BIGNER AND T. BRENT, "EXPRESSION OF $O^6$-ALKYLGUANINE-DNA ALKYLTRANSFERASE IN MER+ AND MER− HUMAN CELL EXTRACTS PROBED WITH SPECIFIC MONOCLONAL ANTIBODIES", *CANCER COMMUNICATIONS*, VOLUME 1, PAGES 323–327, 1989.

Around this same time period, the present inventor also attempted to develop monoclonal antibodies to MGMT using materials which had been partially purified and denatured on glass filters. See D. YAROSH AND J. CECCOLI, "MONOCLONAL ANTIBODIES AGAINST THE HUMAN $O^6$-METHYLGUANINE-DNA METHYLTRANSFERASE", *PROCEEDINGS OF THE AMERICAN ASSOCIATION FOR CANCER RESEARCH*, VOLUME 29, PAGE 1, 1988. Although mouse serum containing the antibodies would recognize MGMT on Western blots, i.e., the antibodies would recognize the denatured protein, they did not recognize the native material. Also, no worthwhile hybridomas were obtained from this work, since the antibodies which were produced had low affinity and were generally not useable.

After their work with denatured MGMT, the Bigner/Brent group turned to the use of synthetic peptide fragments corresponding to different portions of the amino acid sequence of human MGMT to produce polyclonal antibodies to MGMT. Specifically, they used three fragments corresponding to predicted hydrophilic portions of the MGMT molecule and a fourth fragment centered around the cysteine residue which accepts the alkyl group from alkylated DNA. L. OSTROWSKI, C. PEGRAM, M. VON WRONSKI, P. HUMPHREY, X. HE, S. SHIOTA, S. MITRA, T. BRENT AND D. BIGNER, "PRODUCTION AND CHARACTERIZATION OF ANTIPEPTIDE ANTIBODIES AGAINST HUMAN $O^6$-METHYLGUANINE-DNA METHYLTRANSFERASE", CANCER RESEARCH VOLUME 51, PAGES 3339–3344, 1991.

The best that can be said for this work is that it achieved mixed results. Thus, all four polyclonal antibodies were able to precipitate inactive (methylated) MGMT, two of the four recognized MGMT on Western blots, but the other two did not, and only one of the four would precipitate native MGMT. No evidence is presented in the Ostrowski et al. paper that any of the antibodies could be used for single cell staining. Moreover, in terms of large scale, commercial screening of tumor samples, polyclonal antibodies are impractical since individual animals have different immunological responses to a given antigen.

Similar results with polyclonal antibodies raised against synthetic peptide fragments were obtained by Anthony E. Pegg, another leading scientist in the field, and his group. A. E. PEGG, L. WIEST, C. MUMMERT, AND M. E. DOLAN, "PRODUCTION OF ANTIBODIES TO PEPTIDE SEQUENCES PRESENT IN HUMAN $O^6$-ALKYLGUANINE-DNA ALKYLTRANSFERASE AND THEIR USE TO DETECT THIS PROTEIN IN CELL EXTRACTS", CARCINOGENESIS, VOLUME 12, NUMBER 9, PAGES 1671–1677, 1991; and A. E. PEGG, L. WIEST, C. MUMMERT, L. STINE, R. C. MOSCHEL, AND M. E. DOLAN, "USE OF ANTIBODIES TO HUMAN $O^6$-ALKYLGUANINE-DNA ALKYLTRANSFERASE TO STUDY THE CONTENT OF THIS PROTEIN IN CELLS TREATED WITH $O^6$-BENZYLGUANINE OR N-METHYL-N′-NITRO-N-NITROSO-GUANIDINE", *CARCINOGENESIS*, VOLUME 12, NUMBER 9, PAGES 1679–1683, 1991. In this case, six antisera were prepared and all were found to react with MGMT on Western blots. However, none of the antisera "showed any detectable interaction with the native-protein either before or after affinity purification" which Pegg et al. describe as "quite surprising" since relatively hydrophilic sequences were used for the immunization. *CARCINOGENESIS* at 1674 and 1677. Pegg et al. describe the sum and substance of their work as follows: "[T]he development of sensitive and specific immunoassays that can be used to determine the occurrence and intracellular distribution of the alkyltransferase requires the development of more specific reagents. It is possible, but at present unproven, that this may be accomplished by more extensive immunopurification of the present antibodies or by modifying the peptide sequences used for immunization." *CARCINOGENESIS* at 1677.

The polyclonal antibody approach, in this case raised against recombinant human MGMT, is also described in an abstract published in March 1992 by S. M. LEE, J. RAFFERTY, C. Y. FAN, N. THATCHER, AND G. P. MARGISON, "REGIONAL AND CELLULAR HETEROGENEITY OF EXPRESSION OF $O^6$-ALKYLGUANINE-DNA ALKYLTRANSFERASE IN MELANOMA", PROCEEDINGS OF THE AMERICAN ASSOCIATION FOR CANCER RESEARCH, VOLUME 33, MARCH 1992, PAGE 547.

The overall current state of the art was aptly summarized in a review article by Dr. Pegg which recently appeared in the FEDERATION OF AMERICAN SOCIETIES OF EXPERIMENTAL BIOLOGY JOURNAL, VOLUME 6, PAGES 2302–2310 at 2306: "It is apparent that much more work in this area is needed and that there is an urgent need for a method for studying the distribution of alkyltransferase on a cellular basis. This measurement is of major importance because of the role of the alkyltransferase in conferring resistance to chemotherapeutic agents . . . The obvious possibility in this regard is immunohistochemistry, but it remains to be demonstrated that antisera of sufficient specificity and affinity to measure the small amounts of alkyltransferase present in cells can be prepared."

It is to this challenge that the present invention is directed and as demonstrated below, the invention achieves the goal of providing monoclonal antibodies which have sufficient specificity and affinity to detect MGMT in single cell preparations.

SUMMARY OF THE INVENTION

In view of the foregoing state of the art, it is an object of this invention to provide assays for MGMT. More particularly, it is an object of this invention to provide reagents, in particular, monoclonal antibodies for use in assays for MGMT. It is a specific object of the invention to provide assays for detecting MGMT in single cell preparations, as well as reagents for use in such assays. It is a further object of the invention to provide quantitative measures of the levels of MGMT in single cell preparations. It is an additional object of the invention to provide immunoassays for MGMT and reagents for use in such assays.

To achieve the foregoing and other objects, the invention in accordance with certain of its aspects provides monoclonal antibodies which have the ability to recognize MGMT having transferase activity. In particular, the monoclonal antibodies are prepared by immunizing an animal with MGMT which has transferase activity, rather than with denatured MGMT or peptide fragments. As demonstrated by the examples presented below, by means of these monoclonal antibodies, the single cell assays which the art has been seeking for these many years are finally achieved.

Although not wishing to be bound by any particular theory of operation, it is believed that prior workers in the art failed to produce the desired MGMT reagents because they did not take into account the effects of the three dimensional structure of MGMT in determining the response of an animal's immune system to this protein. That is, they followed the conventional wisdom which teaches that antibodies which recognize the native form of an antigen can be successfully raised using denatured antigen or synthetic peptide fragments as the immunogen. See A. M. CAMPBELL, *MONOCLONAL ANTIBODY TECHNOLOGY: THE PRODUCTION ABD CHARACTERIZATION OF RODENT AND HUMAN HYBRIDOMAS*, ELSEVIER, N.Y., 1984, PAGES 88–89; and J. W. GODING, *MONOCLONAL ANTIBODIES: PRINCIPLES AND PRACTICE*, HARCOURT BRACE JOVANOVICH, NEW YORK, 1986, PAGES 28–31.

In accordance with the invention, it has been recognized that the MGMT protein can exist in several structural conformations related to protein folding, each of which is antigenically distinct. This realization has come from various pieces of indirect evidence. First, the MGMT protein is labile and its activity is easily lost at moderate temperatures, but stabilized by the presence of DNA. This suggests that the native protein is easily unwound, but the active conformation can be stabilized by hydrogen binding of key residues to DNA.

Further, a significant activity purification factor is achieved by hydrophobic chromatography using Affigel-Blue and elution with high-salt/1% TRITON X-100, indicating an exposed hydrophobic region in the active protein which might promote instability in aqueous suspension. Moreover, the Stoke's radius from gel filtration is anomalous compared to its molecular weight, suggesting a cigar-shaped compact folding of the active form.

Additional evidence comes from the observation that antibodies raised against homologous MGMT primary amino acid sequences do not make useful histochemical reagents. Also, antibodies raised against the *E. coli* MGMT do not cross-react with the human MGMT, despite the extensive homology in amino acid sequence around the active site, presumably because the folding of the homologous primary sequence is not the same. Further, antibodies prepared in accordance with the invention against the human MGMT were found to have greatly reduced affinity for the mouse MGMT, again despite significant primary amino acid sequence homology.

Along these same lines, the alkylated MGMT protein which results from DNA repair is quickly lost from cells, suggesting a conformational change which targets the protein for proteolytic digestion. MGMT thus appears to easily change its antigenic conformation as part of its biological function and as a consequence of its hydrophobic character.

This indirect evidence has been interpreted in accordance with the invention as meaning that the three dimensional conformation of the MGMT used to immunize an animal plays a central role in determining the properties of the resulting antibodies. Thus, the antibodies of the invention are produced using MGMT having transferase activity, as opposed to denatured MGMT or MGMT polypeptide fragments. The active MGMT has a three dimensional structure different from that of either the inactive form or the fragments and results in antibodies which are able to reliably and accurately recognize MGMT in, among other things, single cell preparations. Prior art antibodies, on the other hand, which were raised against polypeptides, which do not fold in a way similar to the entire molecule, or against denatured protein, which again has a different shape, failed in the critical single-cell-preparation test.

The breakthrough achieved by the invention is thus evident. By using MGMT having transferase activity as the immunogen, monoclonal antibodies are produced against a protein conformation which appears in both cell extracts and in single cell preparations. Accordingly, the antibodies of the invention provide for the first time a practical way to detect MGMT both by way of immunoassays and, most importantly, by single cell staining. As such, the invention allows for, among other things, better patient management, more effective chemotherapy, and improved understanding of the distribution and function of MGMT in normal and malignant cells.

The accompanying figures, which are incorporated in and constitute part of the specification, illustrate preferred embodiments of the invention, and together with the description, serve to explain the principles of the invention. It is to be understood, of course, that both the figures and the description are explanatory only and are not restrictive of the invention.

DESCRIPTION OF THE PREFERRED EMBODIMENTS

As discussed above, the present invention relates to assays for MGMT. Although in most cases, e.g., in clinical applications, the MGMT of interest will be human MGMT, the invention can also be used to detect non-human MGMT in, for example, research studies of the function and distribution of this protein in different cells, organs, and tissues in both normal and diseased states. The invention can also be used in genetic engineering studies and experiments involving the MGMT protein. In addition, the invention can be used to study exogenous MGMT introduced into an organism by gene therapy or protein delivery.

As used herein, the term "$O^6$-methylguanine-DNA methyltransferase" and the abbreviation "MGMT" are each intended to mean the family of homologous proteins, specific forms of which are found in most living organisms, which have the ability to transfer alkyl groups, e.g., methyl groups, from the O-6 position of guanine in alkylated DNA to a cysteine residue of their own polypeptide chain. Depending on the context, this term and abbreviation are also used to refer to individual members of the family.

cDNA for human MGMT has been cloned and the DNA and amino acid sequences published in K. TANO, S. SHIOTA, J. COLLIER, R. S. FOOTE, AND S. MITRA, "ISOLATION AND STRUCTURAL CHARACTERIZATION OF A cDNA CLONE ENCODING THE HUMAN DNA REPAIR PROTEIN FOR $O^6$-ALKYLGUANINE", *PROC. NATL. ACAD. SCI. USA,* VOLUME 87, PAGES 686–690, 1990, the relevant portions of which are incorporated herein by reference. See also H. HAYAKAWA, G. KOIKE, AND M. SEKIGUCHI, "EXPRESSION AND CLONING OF COMPLEMENTARY DNA FOR A HUMAN ENZYME THAT REPAIRS $O^6$-METHYLGUANINE IN DNA, *J. MOL. BIOL.,* VOLUME 213, PAGES 739–747, 1991; B. RYDBERG, N. SPURR, AND P. KARRAN," cDNA CLONING AND CHROMOSOMAL ASSIGNMENT OF THE HUMAN $O^6$-METHYLGUANINE-DNA METHYLTRANSFERASE, *J. BIOL. CHEM.,* VOLUME 265, PAGES 9563–9569, 1990,; and M. A. VON WRONSKI, S. SHIOTA, K. TANO, S. MITRA, D. D. BIGNER, AND T. P. BRENT, "STRUCTURAL AND IMMUNOLOGICAL COMPARISON OF INDIGENOUS HUMAN $O^6$-METHyLGUANINE-DNA METHYLTRANSFERASE WITH THAT ENCODED BY A CLONED cDNA", *J. BIOL. CHEM.,* VOLUME 266, PAGES 1064–1070, 1991, the relevant portions of which are also incorporated herein by reference. Using the cloned cDNA and conventional cell culturing techniques, substantial quantities of human MGMT can be readily obtained. Similar approaches can be used to obtain MGMT for other organisms. In this regard, cloning of cDNA for mouse MGMT has been reported in S. Shiota, M. yon Wronski, K. Tano, D. Bigner, T. Brent and S. Mitra. "CHARACTERIZATION OF cDNA ENCODING MOUSE DNA REPAIR PROTEIN $O^6$-METHYLGUANINE-DNA METHYLTRANSFERASE AND HIGH-LEVEL EXPRESSION OF THE WILD-TYPE AND MUTANT PROTEINS IN *Escherichia coli.,*" *BIOCHEMISTRY* 31:1897–1903, 1992, and for rat MGMT in N. Sakumi, A. Shiraishi, H. Hayakawa and M. Sekiguchi. "CLONING AND EXPRESSION OF cDNA FOR RAT $O^6$-METHYLGUANINE-DNA METHYLTRANSFERASE," NUCLEIC ACIDS RESEARCH 19:5597–5601, 1991, the relevant portions of which are incorporated herein by reference. See also B. RYDBERG, J. HALL, AND P. KARRAN, "ACTIVE SITE AMINO ACID SEQUENCE OF THE BOVINE $O^6$-METHYLGUANINE-DNA METHYLTRANSFEHASE", *NUCLEIC ACIDS RES.,* VOLUME 18, PAGES 17–21, 1990, with regard to the bovine MGMT, the relevant portions of which are also incorporated herein by reference.

Naturally occurring MGMT, as opposed to MGMT produced by genetic engineering techniques, can be used to prepare the monoclonal antibodies of the invention. The genetic engineering approach, however, is clearly preferred in view of the low levels of this protein normally present in cells.

Since the MGMT used to produce the monoclonal antibodies of the invention must have transferase activity, preparation of purified protein suitable for immunization of, for example, a mouse must be performed under conditions where the protein is not denatured, e.g., purification cannot be performed using polyacrylamide-SDS gels as in the prior art. The preferred purification procedure is that disclosed in Yarosh, PCT Patent Publication No. WO90/00598, published Jan. 25, 1990, and Yarosh, U.S. Pat. No. 5,077,211, issued Dec. 31, 1991, the relevant portions of which are incorporated herein by reference.

As described in detail therein, the purification process involves the basic steps of: 1) contacting an aqueous solution containing MGMT with a molecular sieve, 2) eluting the MGMT from the molecular sieve, 3) applying the eluted MGMT to a nucleic acid column, 4) washing the nucleic acid column, and 5) eluting the MGMT from the nucleic acid column. This process has been found to produce homogenous MGMT (as determined by SDS polyacrylamide gel electrophoresis) which has transferase activity. Other purification techniques which produce active MGMT can be used, but the above technique is considered to be the most effective and practical way to obtain the purified protein.

As used herein, the phrase "MGMT having transferase activity" means MGMT which is able to transfer an alkyl group from the O-6 position of guanine to itself. Various activity assays are known in the literature, any of which can be used to make this determination. See, for example, Brent, *Pharmac. Ther.,* supra; Ostrowski et al, *Cancer Research,* Supra; yon Wronski et al., *Cancer Communications,* supra, Fujio et al., *Carcinogenesis,* supra; Aida et al., *Carcinogenesis, supra;* and Watatani et al., *Carcinogenesis, supra.* Assays for this activity which may be developed in the future may also be used for this purpose.

The monoclonal antibodies of the invention are preferably prepared using conventional hybridoma production and antibody purification techniques. See, for example, KOHLER AND MILSTEIN, *NATURE,* VOLUME 256, PAGES 495–497, 1975, and Goding, supra, and Campbell, supra, the relevant portions of which are incorporated herein by reference. Screening of hybridoma clones is preferably performed using active MGMT. Clones which bind to the active protein are subcloned and again screened against the active material to select candidate hybridomas. The final selection of one or more preferred clones is made by employing the monoclonal antibodies produced by the candidate clones in the assay protocol or protocols which are to be performed, e.g., in an immunohistochemical staining protocol and/or an ELISA assay, and selecting those antibodies which perform the best.

In terms of clinical practice, the cells to be assayed are obtained using standard biopsy techniques and can come from essentially any organ or tissue of the body. At present, assays for MGMT are especially important in the case of breast, colon, and brain tumors since the results of the assays can be used to select appropriate treatment protocols. As greater understanding of the function and distribution of MGMT in normal and diseased cells is obtained through the use of the assays of the invention, further predictive applications of the invention will be developed. In terms of research applications of the invention, the cells to be assayed can again come from biopsies, but can also be obtained from tissue culture or other laboratory preparations.

When immunohistochemical assays are performed using the monoclonal antibodies of the invention, the cells to be examined must be fixed to a solid support for microscopy. This may be accomplished by a variety of methods, including brief treatment with organic solvents such as methanol or acetone, or by treatment with 4% glutaraldehyde. Care must be taken not to alter the antigenic properties of the MGMT, and so strong cross-linking agents such as formaldehyde should in general be avoided. In the use of the monoclonal antibodies described in the examples discussed below, fixation by ice-cold acetone for one or two minutes was found to be superior to fixation by a similar treatment with methanol alone. Methanol followed by acetone fixation produced results similar to acetone alone.

MGMT is an intracellular protein and therefore methods must be used to permeabilize cells in order that the monoclonal antibody may traverse the outer membrane to bind to internal MGMT. Acetone fixation forms holes in membranes to some extent. Many detergents can be used to make membranes permeable, including 0.1% saponin, 25 mM octylglucopyranoside, and 0.1% NP-40 or TRITON X-100. While these treatments are approximately equivalent, inclusion of 0.1% TRITON X-100 has been found to be the best permeabilizing agent for use with the monoclonal antibodies described below.

Many incubation procedures may be used to bind the monoclonal antibody to the MGMT in cells, and the particular procedure used will normally be chosen based on practical convenience. In general, incubation at room temperature requires only an hour, while incubation at refrigerated temperatures, e.g., 4° C. or 10° C., requires overnight (e.g., 18 hour) incubation. Higher temperatures, such as 37° C., are normally not preferred.

The incubation is preferably carried out in a buffer having a pH of about 8, since reduced antibody binding has been observed at pH 7.5 (see Table 2 and discussion below). When the readout is performed using a second antibody (see below), the buffer should contain 10% serum derived from the species producing the second antibody to block non-specific binding sites. In the case of a fluorescent readout, the buffer should also contain a reducing agent to minimize background autofluorescence. In addition, the buffer preferably contains the permeabilizing agent which allows the monoclonal antibody to enter the cells and bind to MGMT.

In practice, a staining/buffer solution having the following composition has been found to give the most favorable results: monoclonal antibody at 0.1–1.0 mg/ml in phosphate buffered saline, pH 8, with 0.1% TRITON X-100, 50 mM dithiothreitol and 10% goat serum. This solution is applied as a 50 microliter drop to slides to which the cells have been fixed using ice-cold acetone, covered with a coverslip and incubated for 1 hour at room temperature. The cells are then washed and the monoclonal antibody solution reapplied and incubated at 4° C. overnight.

After washing unbound monoclonal antibody from the cells, the binding of the antibody to cellular MGMT can be detected by a number of methods, including both direct detection of the antibody molecules and indirect detection.

In the direct method, the monoclonal antibody is labeled with, for example, a radioactive tracer which can be detected by overlaying with a photographic emulsion, an imaging molecule which is either fluorescent or directly visible by high-powered microscopy (e.g. gold), or with an enzyme having an activity which can be detected. Binding of the MGMT is then directly detected by assaying for the label.

In the indirect method, a second molecule is used, such as an antibody from another species raised against the isotype of the monoclonal antibody, which contains one of the above labels. Included in the indirect method is the use of binding systems such as the biotin-avidin system, in which the monoclonal antibody is modified with one member of the binding system, and the indirect label is bound to the other member of the binding pair. In the indirect method, the second molecule (e.g. antibody, ligand, etc.) is applied to the monoclonal antibody bound to MGMT, and the amount of the second molecule which becomes bound to the monoclonal antibody is detected after suitable washing steps.

Among the most common detection methods in current use is the indirect method employing goat anti-mouse antibodies linked to an enzyme such as peroxidase or alkaline phosphatase. The binding of these second antibodies is detected by the addition of a substrate which is converted to an insoluble, colored substance by the enzyme and is deposited on the cells at the sites where mouse monoclonal antibody has become bound to the cells. The resulting pattern is then viewed by light microscopy.

Another method and the one which is preferred for use in the present invention employs goat anti-mouse antibodies linked to a fluorescent label, such as fluorescein isothiocyanate (FITC). Binding of the monoclonal antibody is detected in this case by immunofluorescent microscopy in which the sample is excited by a wavelength of light absorbed by the fluorochrome and the sample is examined through a barrier filter which only passes light emitted by fluorescence of the fluorochrome. The emitted photons of light are then recorded either by photographic or digital methods.

In the practice of the invention, the fluorescent method is considered superior to the enzymatic method in that the fluorescent readout has a larger dynamic range so that small differences in the number of monoclonal antibody molecules bound to MGMT may be detected. The enzymatic reactions, on the other hand, are difficult to control so that the colored product is deposited in a relation linear to the amount of bound antibody. Although not preferred, it is to be understood that enzymatic readouts can be used if desired.

As described in the examples below, the best quantification of the binding of monoclonal antibody to MGMT has been achieved using goat anti-mouse antibodies linked to fluorescein isothiocyanate (specifically, DTAF, a congener of FITC) with detection of the fluorescence being performed by a digitizing camera which converts incident photons to numbers. A computer file is then created which contains a record of the number of incident photons for each area of the image. Regions of interest within the image, e.g., images of whole cells, are then quantitated by computer software and comparisons are made with standards so that a conclusion can be drawn as to the level of MGMT in the sample. As demonstrated in the examples, this approach can readily and effectively distinguish between cells having widely different levels of MGMT.

In addition to their application to single cell staining techniques, the monoclonal antibodies of the invention can also be used in immunoassays performed on cell extracts. A variety of assay formats now known or subsequently developed can be used in the practice of these aspects of the invention. A preferred format, as illustrated in the examples presented below, is the sandwich assay. Similarly, a variety of readout techniques now known or subsequently developed can be used in performing the immunoassay. Examples include radioactive, enzyme, and fluorescent readouts. General discussions of immunoassay techniques can be found in a variety of standard texts such as Goding supra, and Campbell, supra, the relevant portions of which are incorporated herein by reference.

Without intending to limit it in any manner, the present invention will be more fully described by the following examples.

EXAMPLE 1

Purification of Human MGMT for Monoclonal Antibody Preparation

An extract of $E.\ coli$ which express the human MGMT gene was prepared by sonication of a 200 ml culture concentrated from 2 liters of broth. The $E.\ coli$ clone was obtained from the Laboratory of Molecular Pharmacology, Division of Cancer Treatment, National Cancer Institute, Bethesda, Md.

Purified human MGMT suitable for preparing monoclonal antibodies was obtained from the MGMT-containing extract following the purification procedures of U.S. Pat. No. 5,077,211, referred to above. Specifically, the debris was removed by centrifugation and the supernatant containing protein at 40 mg/ml was applied to a 4.8×30 cm column of SEPHADEX G-75 at 120 ml/hr with Buffer A (50 mM Tris, pH 8, 50 mM NaCl, 1 mM beta-mercaptoethanol, 1 mM ethylenediaminetetraacetic acid). The optical density at 280 nm of the eluent was monitored and the first peak of optical density was discarded. The second peak of 150 ml at 4.5 mg/ml protein was collected and applied to a 100 ml single-stranded DNA:agarose radial flow column at 400 ml/hr. The column was washed with 400 ml of Buffer A and eluted with a gradient composed of 100 ml of Buffer A and 100 ml of Buffer A containing 1M NaCl. The optical density of the eluent was monitored at 280 nm, and 5 ml fractions were collected. The peak eluted by the gradient, representing pure human MGMT, was collected in 67 ml at 0.7 mg/ml.

The purified MGMT protein produced in this way was found to be homogenous as determined by sodium dodecylsulfate-polyacrylamide gel electrophoresis.

EXAMPLE 2

Determination of Transferase Activity of Human MGMT for Monoclonal Antibody Preparation The activity of the purified human MGMT prepared in Example 1 was assayed using a DNA substrate containing $^3H$-$O^6$-methylguanine prepared by alkylating calf thymus DNA with $^3H$-methylnitrosourea. The MGMT was mixed with substrate in 0.25 ml Methyltransferase Buffer (70 mM Hepes, pH 7.1, 1 mM dithiothreitol, 1 mM ethylenediaminetetraacetic acid, 5% glycerol, 0.1 mg/ml bovine serum albumin) and incubated for 30 minutes at 37° C. The reaction mixture was brought to 5% trichloroacetic acid and heated at 80° C. for 30 minutes to depurinate the DNA and precipitate proteins. The precipitated proteins, including reacted MGMT, were collected on WHATMAN GF/C glass fiber filters, and washed with 5% trichloroacetic acid followed by ethanol. The radioactivity captured on the filters was measured by liquid scintillation counting. The activity of MGMT was calculated from the amount of radioactivity transferred from DNA to protein and captured on the filters, and the specific activity of the $^3H$-methylnitrosourea used to prepare the substrate.

Using the foregoing activity assay, the purified human MGMT prepared in accordance with Example 1 was found to have an activity greater than 200 pmol of $^3H$-methyl groups transferred per mg of purified MGMT protein.

EXAMPLE 3

Preparation of Monoclonal Antibodies to Human MGMT

Two Balb/c female mice 6 weeks old were injected in the flank with 35 micrograms of purified human MGMT, prepared in accordance with Example 1 and tested for activity in accordance with Example 2, which were mixed with Freund's complete adjuvant. After 14, 21, and 28 days the mice were boosted i.p. with 35 micrograms of the purified MGMT mixed with Freund's incomplete adjuvant. After 41 days the mice were boosted i.p. with 35 micrograms purified MGMT without adjuvant.

After 45 days the spleens of both mice were removed, and a mixed cell suspension was prepared and fused with FO myeloma cells (ATCC Accession No. CRL 1646) using 50% low molecular weight PEG in a standard fusion protocol. Hybridomas were selected in HAT media, and primary clones were screened by both ELISA using the native protein and Western blot using the denatured protein. Positive hybridomas were subcloned and screened again by both ELISA and Western blot.

Eight subclones were selected and designated FF2.1, FF2.4, FF2., FF2.10, FF2.13, FF2.15, FF2.16, and FF2.17. The cells were cultured and purified monoclonal antibody was obtained as follows. The hybridoma line was grown to 80–90% confluence in RPMI-1640 media with 15% fetal calf serum, collected by centrifugation and resuspended in RPMI-1640 media without serum but containing ITS supplement (insulin, transferrin and selenium). After 24 hours additional media was added to adjust the cell number to 500,000 per ml. The culture was incubated for 14 to 21 days until the cell viability, as determined by trypan blue dye exclusion, was 40%. The cells were removed by centrifugation and the monoclonal antibody was precipitated by chilling on ice and addition of an equal volume of water saturated with ammonium sulfate. The precipitated proteins were collected by centrifugation, resuspended in and dialyzed against 20 nM Tris pH 7.2. The solution was applied to a column of DEAE-Affigel Blue and washed with the Tris buffer. The bound monoclonal antibodies were then eluted with the same buffer containing 100 mM NaCl. The eluted antibody was collected and dialyzed against PBS overnight, aliquoted, and stored at $-70°$ C.

The monoclonal antibodies were tested in various formats and the results of this testing are presented in Table 1 where the following abbreviations are used: $M_{ab}$=monoclonal antibody; +=strong response; ±=weak or variable response; —=no response; NT=not tested; ELISA=enzyme-linked immunoassay in which MGMT is bound to the wells of a microliter plate and antibody is added to the wells thereafter; SAND ELISA=sandwich ELISA using polyclonal rabbit anti-MGMT antibodies (see Example 7 below); MEMTEST=MGMT covalently linked to a MEMTEST membrane and tested in a dot-blot format; WEST BLOT=Western blot of denatured MGMT; Nat=native (active) human MGMT; Denat=denatured human MGMT obtained by boiling native human MGMT in 1% SDS; and Form=formalin fixed human MGMT obtained by incubating native human MGMT at 37° C. for 60 min in 4% formaldehyde. As shown in this table, monoclonal antibodies which reacted against native MGMT generally faired poorly against denatured MGMT.

The screening of hybridomas from the FF panel described in Table 1 resulted in narrowing the candidates to FF2.4, FF2.10 and FF2.16. These antibodies were tested on three sets of Mer+ (MGMT positive) and Mer− (MGMT negative) cell lines matched by tissue type. Only FF2.16 consistently showed a significant difference in binding between the Mer+ and Mer− cells, as determined by computerized image analysis of fluorescent stained slides (see Example 4 below).

Other monoclonal antibodies were prepared using a combination of purified human MGMT and synthesized polypeptides corresponding to the 10 amino-terminal and 10 carboxy-terminal amino acids of human MGMT. These latter materials were included for the purpose of obtaining clones against the peptides. Subsequent work showed that serum produced by immunization with just the peptides would not recognize native MGMT, so that in terms of producing antibodies to the complete protein only the purified human MGMT functioned as an effective immunogen in these experiments.

The immunization protocol followed in this case was as follows. A Balb/c female mouse 6 weeks old was injected in the flank with 18 micrograms of human MGMT purified as in Example 1 and tested for activity in accordance with Example 2, which was mixed with Freund's complete adjuvant. After 14 days the mouse was boosted with 50 micrograms of each polypeptide. After 28 and 39 days the mouse was boosted i.p. with 25 micrograms of purified human MGMT mixed with 50 micrograms of each of the polypeptides in Freund's incomplete adjuvant. After 88 days the mouse was boosted with 50 micrograms of purified human MGMT i.p. without adjuvant, and on the 92nd day the spleen was removed.

A suspension was prepared and the spleen cells were fused to FO myeloma cells using 50% low molecular weight PEG in a standard fusion protocol. Hybridomas were selected using HAT media, and primary clones were screened by ELISA using the same purified human MGMT as in the immunization. Positive hybridomas were subcloned and again screened both by ELISA and Western blot using the purified human MGMT. Culturing of the selected hybridomas and purification of the monoclonal antibodies was performed as described above for the FF panel.

Two monoclonal antibodies, designated DF4.2 and DF13.1, were identified by these experiments. These antibodies showed strong affinity in the ELISA assay using native MGMT but little reaction in the Western blot. Their binding to MGMT immobilized on membranes was also found to be greatly diminished by denaturing or formalin fixation of the protein. Had only Western blotting or screening of formalin-fixed tissue been used, these two monoclonal antibodies would not have been detected.

Properties of the DF4.2 and DF13.1 monoclonal antibodies are set forth in Table 2 where the affinity of each monoclonal antibody ($M_{ab}$) for the antigen was determined by ELISA from the slope of the linear portion of the curve of $OD_{405}$ versus micrograms of antibody. In constructing this table, the affinity of each antibody at pH 8 against rHuMGMT (recombinant human MGMT) was set at 1.00 and the slopes under other conditions were compared to the slope under these conditions. The third column of the table compares the affinities of the two antibodies under the various conditions.

As shown in Table 2, the DF13.1 antibody has a lower affinity than the DF4.2 antibody. On the other hand, the DF13.1 antibody has been found to have broader specificity than the DF4.2 antibody and thus is particularly useful in immunoassay applications, although the DF4.2 antibody can also be used in this application. Both of these monoclonal antibodies are considered suitable for use in immunohistochemical assays, with the DF13.1 antibody being somewhat more preferred. As between these antibodies and the FF2.16 antibody, the DF13.1 antibody is considered the preferred choice.

A deposit of the hybridoma which produces the DF13.1 antibody (hybridoma cell line DF13.1) has been made with the American Type Culture Collection, Rockville, Maryland, and has been assigned accession number HB 11046. This deposit was made on May 20, 1992 under the Budapest Treaty on the International Recognition of the Deposit of Microorganisms for the Purposes of Patent Procedure. It is to be understood that variants of hybridoma cell line DF13.1, produced intentionally or spontaneously, e.g., mutants, which continue to produce monoclonal antibody to MGMT having transferase activity, comprise part of the invention and can be used in the various assays described herein.

EXAMPLE 4

Quantitation of Human MGMT in Liver Cells Using Monoclonal ANtibodies DF13.1 and FF2.16

Frozen human liver sections on glass slides were fixed with 0.2% glutaraldehyde for 10 minutes at room temperature, and hydrated with phosphate buffered saline (PBS) for 5 minutes. The slides were incubated in 0.025% Trypsin/PBS/0.5% Tween for 40 minutes at 37° C., and blocked with PBS/0.5% Tween/10% goat serum for 30 minutes. After washing with PBS, the slides were incubated with monoclonal antibody DF13.1 or FF2.16 at 1 mg/ml, or no antibody, in PBS/0.05% Tween/10% goat serum for 60 minutes at 25° C., washed, and the antibody was then reapplied for incubation overnight at 4° C.

After the overnight incubation, the slides were washed with PBS/0.05% Tween, incubated with the second antibody (goat anti-mouse linked to DTAF) in PBS/0.5% Tween/10% human serum for 60 minutes at 25° C. After washing with PBS and dH$_2$O, the slides were mounted with VECTASHIELD (Vector Laboratories, Burlingame, Calif.), and stored at −20° C.

Five slides containing beads with either $1.8 \times 10^6$, $4.3 \times 10^5$, $18 \times 10^5$, $6.2 \times 10^4$, or no FITC molecules per bead (Flow Cytometry Standards Corporation, N.C., USA) were used as standards. This range of bead fluorescence matches that usually encountered in cell samples.

The immunofluorescence of the standards and the cells was viewed using a NIKON B2-A filter set with an IR-cut filter. The images were digitized at 600× magnification using a Photometrics STAR I CCD camera connected to the cameraport of a NIKON Diaphot phase-contrast microscope in combination with image capture software (Photometrics, Tucson, Ariz.). The optimum grey value range was set through automatic windowing (DISPLAY/AUTO) by examining the bead standards with the lowest (minimum) and highest (maximum) concentration of FITC molecules. This matches the most appropriate portion the 4096-step dynamic range of the CCD camera to the 256 grey-scale range of the image file, allowing a linear camera response over the range likely to be found in cell and tissue samples. The minimum and maximum for the beads were found to be 100 and 300, respectively. Automatic windowing was disengaged (DISPLAY/AUTO) and the windows were set (DISPLAY/WINDOW) at 100/300 and kept constant throughout the analysis.

At least two different ten second exposures were taken for the beads and each slide (CAMERA/EXPOSE), and the images stored as .TIF files (ARCHIVES/TIFF SAVE) on a 1.4 Megabyte 3.5" disc using an IBM-clone 386 PC.

The TIFF (tagged-image format files) images were retrieved using the computer image analysis program OPTIMUS (Bioscan, Seattle, Wash.) (FILE/OPEN). Using the "area icon" feature of this program, regions of interest (ROIs) were identified. The first ROI consisted of either a single cell or multiple cells. A second ROI was designated and consisted of a selected portion of the background. The integrated gray value and the area was obtained for each ROI.

In order to calculate an integrated grey value per cell, the intensity of the background per unit area was determined and subtracted from each unit area of the cell-containing ROI. A "net value" was also determined by subtracting the integrated grey value per cell for the "no antibody" control from the integrated grey values per cell obtained for the test monoclonal antibodies. Finally, "FITC Equivalent" values were determined by fitting a regression line to the bead standards and using the slope of that line to convert net values to FITC equivalent values.

The results are shown in Table 3 where the regression line obtained for the bead standards had a slope of $4.5 \times 10^{-4}$ FITC molecules per grey value ($r^2$ value (fit)=0.997). As demonstrated by these results, the monoclonal antibodies of the invention, i.e., antibodies produced using human MGMT having transferase activity, successfully provide quantitative measures of the levels of human MGMT in single cell preparations.

EXAMPLE 5

Quantitation of Human MGMT in MER+ and MER− Cells Using Monoclonal Antibody DF4.2

Human tumor cells with either the Mer+ phenotype (containing MGMT) or the Mer− phenotype (deficient in MGMT) were grown on tissue culture slides, and fixed with methanol for 10 minutes followed by ice-cold acetone for 2 minutes. Following hydration with phosphate buffered saline (PBS) for 5 minutes, the slides were treated with 0,025% trypsin in PBS/0.1% saponin for 40 minutes at 37° C., and blocked with PBS/0.1% saponin/10% goat serum for 30 minutes. After washing with PBS, the slides were incubated with 100 micrograms/ml of the monoclonal antibody DF4.2, or no antibody (control) for 60 minutes at 25° C., washed, and incubated with the same antibody overnight at 4° C.

The slides were then washed with PBS, incubated with the second antibody (goat anti-mouse linked to the fluorescent label DTAF) in PBS/0.1% saponin/10% human serum for 60 minutes at 25° C. After washing with PBS and dH$_2$O, the slides were mounted with VECTASHIELD and stored at −20° C. Image analysis was performed as described in Example 4.

The results are shown in Table 4. As shown therein, the DF4.2 monoclonal antibody, prepared using human MGMT having transferase activity, was able to reliably distinguish the Mer+ phenotype from the Mer− phenotype in a variety of cell types. Moreover, quantitative measures of the MGMT levels in these cells were readily obtained using the assay techniques of the invention.

EXAMPLE 6

Immunohistochemical Assays Using Monoclonal Antibodies DF4.2, DF13.1 AND FF2.16

Using the staining and recording techniques described in Example 4, digitized images of human MGMT levels within various cells were obtained using monoclonal antibodies DF4.2, DF13.1, and FF2.16.

The results are shown in FIGS. 1–3 and the cell types and monoclonal antibodies used in preparing these figures are summarized in Table 5.

The HT29 cells used in FIG. 1 are Mer+colon adenocarcinoma cells containing human MGMT and as shown in panels A, B, and C of this figure, each of monoclonal antibodies DF4.2, DF13.1, and FF2.16 stained these cells, with the FF2.16 and DF13.1 antibodies producing images having the highest contrast. BE cells, on the other hand, are Mer− colon carcinoma cells lacking human MGMT and thus as shown in FIG. 1D, monoclonal antibody DF13.1 does not stain this cell type. Similar results (not shown) are obtained with the DF4.2 and FF2.16 antibodies when applied to BE cells.

FIG. 2 illustrates use of the invention to distinguish between diseased and non-diseased states. FIG. 2A shows cells from a normal human breast where the level of MGMT is relatively low. FIG. 2B shows the results for cells taken from a patient having fibrocystic disease which is considered benign. The MGMT levels are somewhat higher, but not as high as in FIGS. 2C and 2D.

Figure 1A:
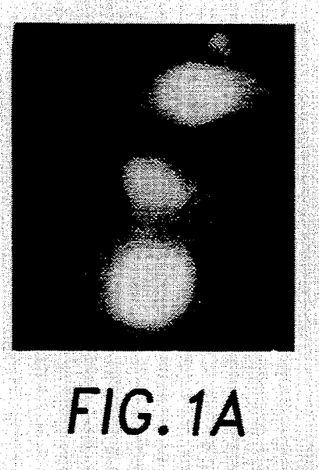
FIGS. 1A–1D, 2A–2D, and 3A–3D are digitized images of cellular preparations which have been immunohistochemically stained using the monoclonal antibodies to human MGMT of the present invention.
Figure 1B:
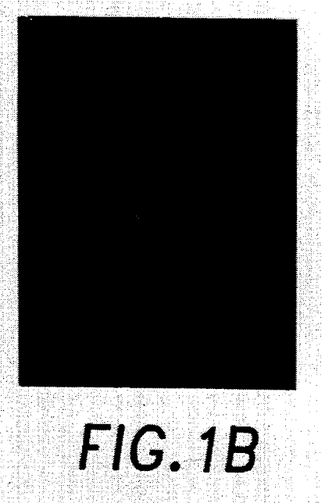
Figure 1C:
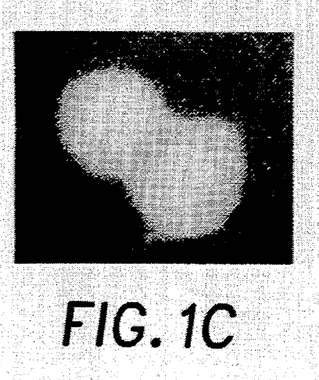
Figure 1D:
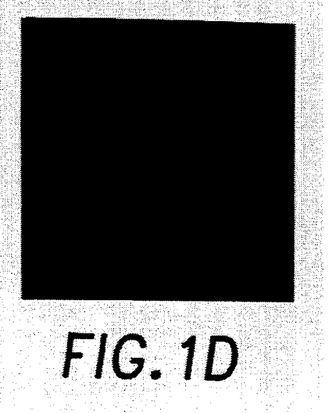
Figure 2A:
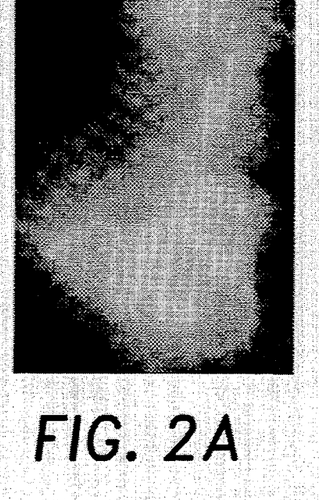
Figure 2B:
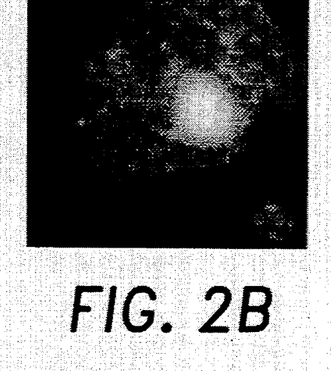
Figure 2C:
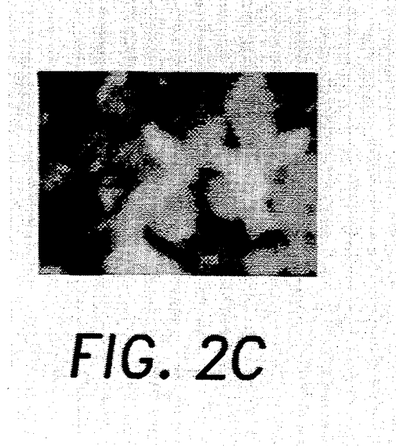
Figure 2D:
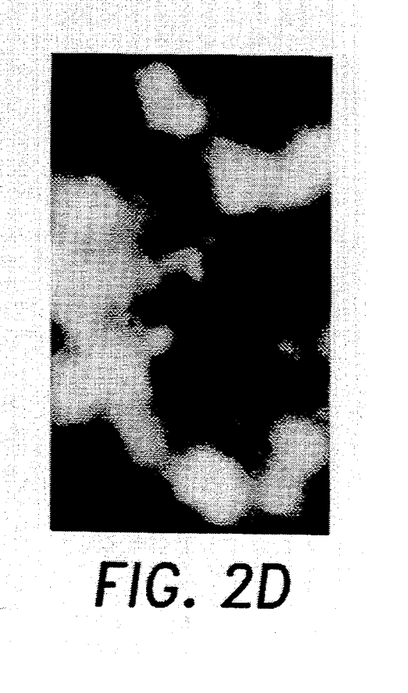
Figure 3A:
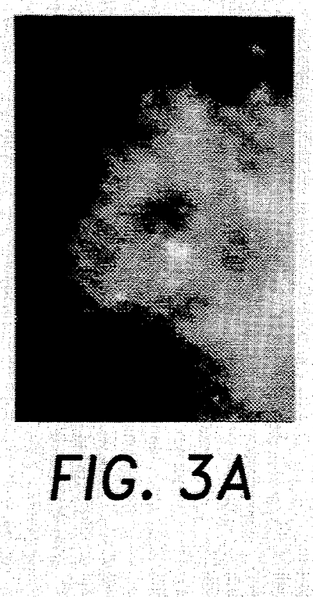
Figure 3B:
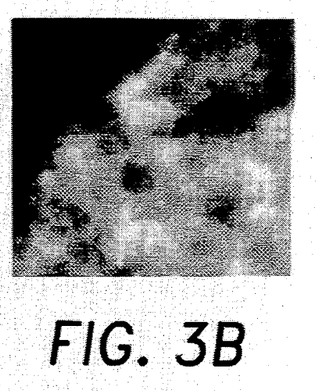
Figure 3C:
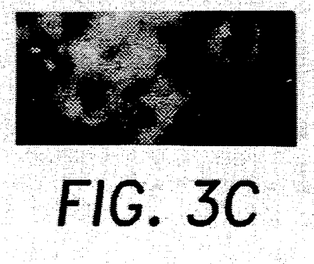
Figure 3D:
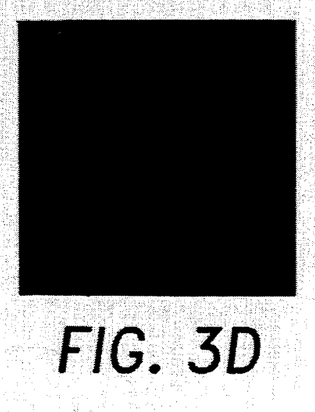

FIG. 2C shows cells obtained from a patient suffering from fibroadenoma, a precursor to breast carcinoma which is considered malignant. Plainly, the MGMT levels are much higher in this figure. Finally, FIG. 2D shows typical cells from a malignant breast carcinoma. As these figures make clear, the levels of MGMT rise significantly as a patient moves from a non-diseased state (FIG. 2A) through to a full malignant state (FIG. 2D) and the assay of the invention can be readily used to follow the progression.

FIG. 3 shows a comparison between the monoclonal antibodies of the invention, specifically, antibodies DF4.2, DF13.1, and FF2.16, and monoclonal antibody G1204 which recognizes an outer protein of Neisseria gonorrhoeae. The cells used in these experiments were human liver cells which are of the Mer+ phenotype. These cells do not contain the Neisseria gonorrhoeae outer protein and thus antibody G1204 serves as a negative control. As shown in this figure, the antibodies of the invention strongly stain the liver cells while the G1204 antibody does not.

EXAMPLE 7

Immunoassays Using Monoclonal Antibody DF13.1

A sandwich ELISA assay was performed using a polyclonal antibody to human MGMT ($P_{ab}$ 90-1314) and monoclonal antibody DF13.1.

The polyclonal antibody was prepared as follows. Two New Zealand white rabbits were each inoculated in the flank with 180 micrograms of purified human MGMT prepared in accordance with Example 1 which were mixed with Freund's complete adjuvant. After 14 days, the rabbits were boosted with 180 micrograms of purified human MGMT in incomplete Freund's adjuvant. After 56 and 63 days, the rabbits were boosted with 200 micrograms of purified human MGMT mixed with 200 micrograms of a 50/50 mixture of the polypeptides used in the preparation of the DF panel of monoclonal antibodies. After 78 days the rabbits were exanguinated and the IgG fraction purified from the pooled serum to obtain the desired polyclonal antibody ($P_{ab}$ 90-1314).

For the sandwich ELISA, Pab 90-1314 in 50 mM sodium acetate, pH 5, was oxidized with 10 mM $NaIO_4$ for 30 minutes, and then one-tenth volume ethylene glycol was added and the antibody dialyzed overnight against the same buffer. The antibody was uniformly oriented onto an ELISA plate coated with hydrazine at 50 micrograms per well overnight at 4° C., and the plate blocked with 1% bovine serum albumin in PBS.

Human MGMT, either as purified native protein obtained using the procedures of Example 1 or in cell extracts, was added to the plate. HT29 cells, a colon adenocarcinoma line, and CEM cells, a T-cell leukemia line, were used to prepare the cell extracts. The cells were grown in culture, extracts were prepared, and parallel transferase activity and sandwich ELISA assays were performed on the extracts.

The sandwich ELISA assay was performed by incubating the MGMT or cell extract with the polyclonal antibody for 60 minutes at room temperature and then washing unbound antigen from the plate. DF13.1 was then added, incubated for 60 minutes at room temperature and then washed from the plate. Goat anti-mouse IgG antibodies linked to alkaline phosphatase were added, incubated for 30 minutes, and then washed from the plate. The plates were developed with 1 mg/ml p-nitrophenylphosphate, and read by an ELISA plate reader at 405 nm. The activity assay was performed as in Example 2.

Figure 4:
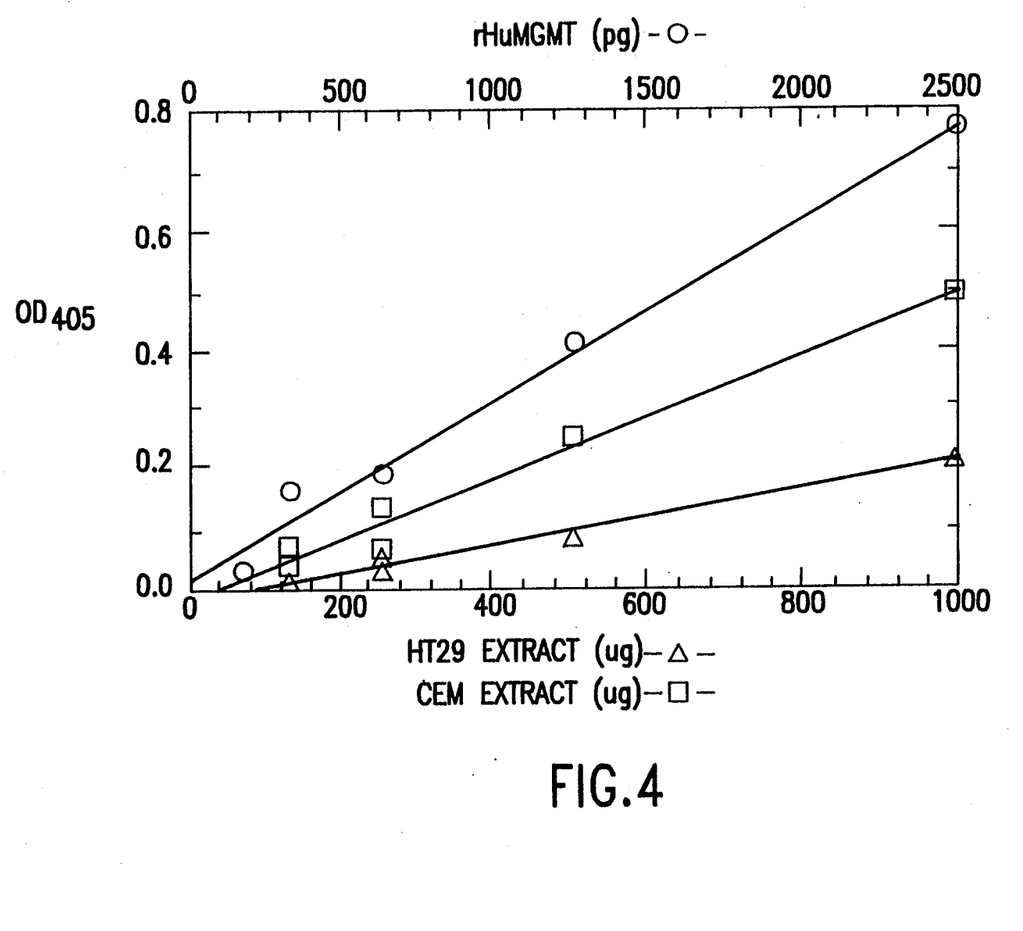
FIG. 4 is a graph illustrating the application of the monoclonal antibodies of the invention to a sandwich ELISA assay for human MGMT. Optical density at 405 nm is plotted along the vertical axis; picograms of purified human recombinant MGMT (rHuMGMT) are plotted along the upper horizontal axis (circle data points); and micrograms of cell extract for HT29 cells (triangular data points) and CEM cells (square data points) are plotted along the lower horizontal axis.

FIG. 4 shows the linear relationships between $OD_{405}$ and MGMT levels which were obtained with this assay both for the purified MGMT and the cell extracts. Table 6 shows the excellent correlation between the activity assay results and the sandwich ELISA results. This example thus demonstrates that the monoclonal antibodies of the invention can be successfully used to perform conventional immunoassays for human MGMT.

Although specific embodiments of the invention have been described and illustrated, it is to be understood that modifications can be made without departing from the invention's spirit and scope. For example, in addition to their use in assays for MGMT, the monoclonal antibodies of the invention can also be used in various MGMT purification systems, e.g., to prepare an antibody affinity column for MGMT. A variety of other modifications which do not depart from the scope and spirit of the invention will be evident to persons of ordinary skill in the art from the disclosure herein. The following claims are intended to cover the specific embodiments set forth herein as well as such modifications, variations, and equivalents.

TABLE 1

RELATIVE ANTIBODY AFFINITY FOR HUMAN MGMT IN VARIOUS SCREENING FORMATS

| $M_{ab}$ | ELISA | | | SAND ELISA | | MEMTEST | | | WEST BLOT |
|---|---|---|---|---|---|---|---|---|---|
| | Nat | Denat | Form | Nat | Denat | Nat | Denat | Form | |
| FF2.1 | − | − | ± | NT | NT | − | − | − | ± |
| FF2.4 | ± | − | ± | − | − | ± | − | − | ± |
| FF2.8 | − | − | ± | − | − | NT | NT | − | ± |
| FF2.10 | ± | − | − | ± | + | ± | − | − | ± |
| FF2.13 | ± | − | − | ± | NT | − | − | − | ± |
| FF2.15 | ± | − | − | ± | NT | − | − | − | ± |
| FF2.16 | ± | − | − | − | NT | ± | ± | − | ± |
| FF2.17 | ± | − | − | − | NT | − | − | − | NT |

TABLE 2

RELATIVE MONOCLONAL ANTIBODY AFFINITY BY ELISA

| | Monoclonal Antibody | | DF13.1 |
|---|---|---|---|
| Antigen | DF4.2 | DF13.1 | DF4.2 |
| rHuMGMT | 1.00 | 1.00 | 0.17 |
| rMuMGMT (mouse)* | 0.19 | 0.17 | 0.67 |
| pH 6.5 | 1.14 | 1.19 | 0.13 |
| pH 7.0 | 1.09 | 1.34 | 0.15 |
| pH 7.5 | 0.59 | 0.06 | 0.01 |
| formalin-rHuMGMT | 0.46 | 0.61 | 0.23 |

TABLE 2-continued

RELATIVE MONOCLONAL
ANTIBODY AFFINITY BY ELISA

|  | Monoclonal Antibody |  | DF13.1 |
|---|---|---|---|
| methylated-rHuMGMT | 1.29 | 0.72 | 0.13 |

*Slope of ng rMuMGMT v. OD compared at fixed $M_{ab}$ concentration.

TABLE 3

QUANTITATION OF HUMAN MGMT IN LIVER CELLS

| Sample | Integrated Grey Value per Cell | Net Value | FITC Equivalent |
|---|---|---|---|
| Bead Standards (FITC molecules/bead): | | | |
| $1.8 \times 10^6$ | 796.2 | 795.1 | |
| $4.3 \times 10^5$ | 142.8 | 141.7 | |
| $1.8 \times 10^5$ | 51.1 | 50.0 | |
| $6.2 \times 10^4$ | 11.9 | 10.8 | |
| 0 | 1.1 | — | |
| Monoclonal Antibodies: | | | |
| DF13.1 | 1061.7 | 154.0 | $3.4 \times 10^5$ |
| FF2.16 | 994.5 | 86.0 | $1.9 \times 10^5$ |
| NONE | 907.7 | — | |

TABLE 4

$M_{ab}$ BINDING TO MER+ AND MER− PHENOTYPE
HUMAN TUMOR CELLS USING THE DF4.2
MONOCLONAL ANTIBODY

| Cell Line | Mer Phenotype | Net Integrated Grey Value per Cell | FITC Equivalent |
|---|---|---|---|
| Colon carcinoma lines: | | | |
| HT29 | + | 11.24 | 24,978 |
| BE | − | 3.75 | 8,333 |
| Brain tumor lines: | | | |
| T98 | + | 4.48 | 9,955 |
| A1235 | − | 0 | 0 |
| Lung cancer lines: | | | |
| A549 | + | 8.88 | 19,733 |
| A427 | − | 0.75 | 1,667 |

TABLE 5

| FIG. | Sample | $M_{ab}$ |
|---|---|---|
| 1A | HT29 cells | FF2.16 |
| 1B | HT29 cells | DF4.2 |
| 1C | HT29 cells | DF13.1 |
| 1D | BE | DF13.1 |
| 2A | Normal Breast | DF4.2 |
| 2B | Fibrocystic disease | DF4.2 |
| 2C | Fibroadenoma | DF4.2 |
| 2D | Carcinoma | DF4.2 |
| 3A | Human Liver Cells | DF4.2 |
| 3B | Human Liver Cells | FF2.16 |
| 3C | Human Liver Cells | DF13.1 |

TABLE 5-continued

| FIG. | Sample | $M_{ab}$ |
|---|---|---|
| 3D | Human Liver Cells | G1204 |

TABLE 6

COMPARISON BETWEEN MGMT ACTIVITY ASSAY
AND SANDWICH ELISA USING THE DF13.1
MONOCLONAL ANTIBODY

| Cell Line | Activity Assay | Sandwich ELISA |
|---|---|---|
| HT29 | 91.7 ± 18.0 (N = 8) | 92.2 ± 22.1 (N = 13) |
| CEM | 129.2 ± 34.3 (N = 6) | 154.3 ± 51.6 (N = 9) |

What is claimed is:

1. An assay for detecting human $O^6$-methylguanine-DNA methyltransferase (MGMT) in human cells comprising:

(a) fixing and permeabilizing the cells;

(b) exposing the fixed and permeabilized cells to a monoclonal antibody for human MGMT under conditions where the monoclonal antibody can bind to human MGMT present in the cells to form antibody-antigen complexes, said monoclonal antibody being prepared using an immunogen comprising human MGMT having transferase activity and said monoclonal antibody being selected by binding of the monoclonal antibody to human MGMT having transferase activity; and (c) detecting antibody-antigen complexes in the fixed and permeabilized cells so as to provide for the detection of human MGMT.

2. The assay of claim 1 wherein the MGMT having transferase activity is prepared by contacting an aqueous solution of MGMT having transferase activity with a molecular sieve, eluting the MGMT from the molecular sieve, applying the eluted MGMT to a nucleic acid column, washing the nucleic acid column, and eluting the MGMT from the nucleic acid column.

3. The assay of claim 1 wherein the antibody-antigen complexes are detected fluorescently.

4. The assay of claim 3 wherein a digitized image of the fluorescence of the fixed and permeabilized cells is obtained.

5. The assay of claim 4 wherein a numerical value indicative of the number of antibody-antigen complexes present in the fixed and permeabilized cells is obtained from the digitized image.

6. The assay of claim 1 wherein the monoclonal antibody is produced by hybridoma cell line DF13.1 having deposit accession number ATCC HB-11046.

7. Hybridoma cell line DF13.1 having the deposit accession number ATCC HB-11046.

8. The monoclonal antibody produced by hybridoma cell line DF13.which has the deposit accession number ATCC HB-11046.

* * * * *